United States Patent
Koman et al.

(10) Patent No.: US 6,362,318 B1
(45) Date of Patent: Mar. 26, 2002

(54) PROTEIN CALLED EPIL/PLACENTIN, PROCESS FOR THE PREPARATION OF THIS PROTEIN AND PHARMACEUTICAL COMPOSITION CONTAINING SUCH, DNA CODING FOR SAID PROTEIN

(76) Inventors: Ahmet Koman, 5 Grand Rue, 78240 Chambourcy; Dorine Chassin, 126 Boulevard de la Liberation, 94300 Vincennes; Dominique Bellet, 18 Rue Diderot, 92170 Vanves, all of (FR)

( * ) Notice: Subject to any disclaimer, the term of this patent is extended or adjusted under 35 U.S.C. 154(b) by 0 days.

(21) Appl. No.: 09/599,564

(22) Filed: Jun. 23, 2000

Related U.S. Application Data

(62) Division of application No. 09/174,465, filed on Oct. 19, 1998, now Pat. No. 6,180,364, which is a division of application No. 08/482,842, filed on Jun. 7, 1995, now Pat. No. 5,910,480.

(30) Foreign Application Priority Data

Jun. 13, 1994 (FR) ............................................. 94 07191

(51) Int. Cl.[7] ........................ C07K 16/00; C07K 16/22; C07K 16/26

(52) U.S. Cl. .............................. 530/388.24; 530/387.1; 530/388.1; 530/388.5; 530/389.1; 530/389.2

(58) Field of Search ........................... 530/387.1, 388.1, 530/388.15, 388.24, 389.1, 389.2

(56) References Cited

FOREIGN PATENT DOCUMENTS

| JP | 48-030370 | 9/1973 |
|---|---|---|
| SU | 273369 | 6/1970 |

OTHER PUBLICATIONS

"Active Preparation Form Human Placental Tissue", (Database Biosis–Abstract), vol. 5 pp. 120–122 (1969).
"Amino Acid Composition of New Blood Substituted from the Placenta", Altunyan et al. (Chem. Abstracts), vol. 78, No. 22 (Jun. 4, 1973).
French Preliminary Search Report; Date of completion of search: Feb. 6, 1995.
Mikayama et al, Molecular cloning and functional expression of a cDNA encoding gycosylation–inhibiting factor, Nov. 1993, Proc. Natl. Acad. Sci, USA vol. 90: 10056–10060.*
Voet et al., Biochemistry I, 1990, pp. 126–230.*
Attwood et al, The Babel of Bioinformatics, 2000, Science vol. 290 No. 5491: 471–473.*
Kuby et al., 1994, Immunology, second edition, pp. 85–96.*
Glimcher et al, Fine specificity of cloned insulin–specific T cell hybridomas: evidence supporting a role for tertiary conformation, Dec. 1983, J. Immunology 131(6): 2868–74.*
Horiuchi et al, Expression of insulin–like growth factor II by a gastric carcinoma associated with hypoglycemia, 1994, Virchow Arch 424(4): 449–52.*
Coleman et al, Effects of amino acid sequence changes on antibody–antigen interaction, 1994, A structural view of immune recognition by antibodies, pp. 33–36.*

* cited by examiner

*Primary Examiner*—Christina Y. Chan
*Assistant Examiner*—Phuong Huynh
(74) *Attorney, Agent, or Firm*—Burns, Doane, Swecker & Mathis, L.L.P.

(57) ABSTRACT

The subject of the invention is a new protein called EPIL or placentin, its analogs ing EPIL/placentin-type activity, obtained by deletion and/or substitution. The tion also concerns a DNA molecule coding for a EPIL/placentin-type polypeptide. It ly concerns a pharmaceutical composition containing EPIL/placentin or a /placentin analog.

4 Claims, 4 Drawing Sheets

| | | | | | | |
|---|---|---|---|---|---|---|
| agt | ctg | gag | ccc | aga | agg | gac | aca | cca | gca | cag | tct | ggt | agg | cta | cag | caa | gtc | tct | 60 | agt ctg gag ccc aga agg gac aca cca gca cag tct ggt agg cta cag caa gtc tct 60
Ser Leu Glu Pro Arg Arg Asp Thr Pro Ala Gln Ser Gly Arg Leu Gln Gln Val Ser aaa gaa agg ctg aga aca ccc aga gag ttc agg tcc agg ATG GCC AGC CTG TTC 120
Lys Glu Arg Leu Arg Thr Pro Arg Glu Phe Arg Ser Arg Met Ala Ser Leu Phe CGG TCC TAT CTG CCA GCA ATC TGG CTG CTG AGC CAA CTC CTT AGA GAA AGC CTA GCA 180
Arg Ser Tyr Leu Pro Ala Ile Trp Leu Leu Ser Gln Leu Leu Arg Glu Ser Leu Ala GCA GAG CTG AGG GGA TGT GGT CCC CGA TTT GGA AAA CAC TTG CTG TCA TAT TGC CCC ATG 240
Ala Glu Leu Arg Gly Cys Gly Pro Arg Phe Gly Lys His Leu Leu Ser Tyr Cys Pro Met CCT GAG AAG ACA TTC ACC ACC ACC CCA GGA GGG TGG CTG CTG GAA TCT GGA CGT CCC AAA 300
Pro Glu Lys Thr Phe Thr Thr Thr Pro Gly Gly Trp Leu Leu Glu Ser Gly Arg Pro Lys GAA ATG GTG TCA ACC TCC AAG AAC AAA GAT GGA CAA GCC TTA GGT ACG ACA TCA GAA TTC 360
Glu Met Val Ser Thr Ser Lys Asn Lys Asp Gly Gln Ala Leu Gly Thr Thr Ser Glu Phe

FIGURE 1A

```
ATT CCT AAT TTG TCA CCA GAG CTG AAG AAA CCA CTG TCT GAA GGG CAG CCA TCA TTG AAG
Ile Pro Asn Leu Ser Pro Glu Leu Lys Lys Pro Leu Ser Glu Gly Gln Pro Ser Leu Lys     420

AAA ATA CTT TCC CGC AAA AAG AGA AGT GGA CGT CAC AGA TTT GAT CCA TTC TGT TGT
Lys Ile Ile Ser Arg Lys Lys Arg Ser Gly Arg His Arg Phe Asp Pro Phe Cys Cys         480

GAA GTA ATT TGT GAC GAT GGA ACT TCA GTT AAA TTA TGT ACA tag tag agt aat cat gga
Glu Val Ile Cys Asp Asp Gly Thr Ser Val Lys Leu Cys Thr Xaa Xaa Ser Asn His Gly     540 ctg gac atc tca tcc att ctc ata tgt att ctc aat gac aaa ttc act gat gcc caa tta
Leu Asp Ile Ser Ser Ile Leu Ile Cys Ile Leu Asn Asp Lys Phe Thr Asp Ala Gln Leu     600 aat gat tgc tgt tta
Asn Asp Cys Cys Leu                                                                  615
```

FIGURE 1B

...5'aggtcagttctatttttatttcatctaagcaaaggacattaaaaattaccattatttttagtaagcataaaatagtattaca
ggaggaaagttaagaaaaagaagtagaacaaccaaattcaaaacaagcaaagtgcagcagcacattgggagcaaagaggatatgag
agtgtgggtagggcaagtaggagaggagactaaataagaactgagg gagaaagttccttgtaggtgggtgggaaggggtgactgacac
cattgacgccaaagctgagtatagccctaagccaaataatgcctgatgaaggcatgcagaaag Exon 1

1   CAGTCTGGAGCCCAGAAGGGACACACCAGCACACAGTCTGGTAGGCTACAGCAGCAAGTCTCTAAAGAAAGGCTGAGAACACCCAGAAC
    AGGAGAGTTCAGGTCCAGG

106 ATG GCC AGC CTG TTC CGG TCC TAT CTG CCA GCA ATC TGG CTG CTG CTG AGC   CAA CTC CTT AGA
    Met Ala Ser Leu Phe Arg Ser Tyr Leu Pro Ala Ile Trp Leu Leu Leu Ser   Gln Leu Leu Arg
    -17                                                             -1    1   B-chain 169 GAA AGC CTA GCA GCA GAG CTG AGG GGA TGT GGT CCC CGA TTT GGA AAA CAC TTG CTG TCA TAT TGC
5   Glu Ser Leu Ala Ala Glu Leu Arg Gly Cys Gly Pro Arg Phe Gly Lys His Leu Leu Ser Tyr Cys 235 CCC ATG CCT GAG AAG ACA TTC ACC ACC CCA GGA TGG CTG|CTG GAA TCT GGA CGT CCC AAA G
27  Pro Met Pro Glu Lys Thr Phe Thr Thr Pro Gly Trp Leu|Leu Glu Ser Gly Arg Pro Lys
                                                      C-peptide

FIGURE 2A

Intron 1   gtgagccctgactaccaaacaatcagaatgagggctgaaaaaaca ...
           acatgaatgttttcctcacctttcattcctctctttacttcacag Exon 2
302  AA ATG GTG TCA ACC TCC AAC AAC AAA GAT GGA CAA AAC GCC TTA GGT ACG ACA TCA GAA TTC ATT CCT
 69     Met Val Ser Thr Ser Asn Asn Lys Asp Gly Gln Asn Ala Leu Gly Thr Thr Ser Glu Phe Ile Pro 367  AAT TTG TCA CCA GAG CTG TCT GAA AAA CCA TCA GGG CAG CCA TCA TTG AAG AAA ATA ATA CTT|
 71  Asn Leu Ser Pro Glu Leu Ser Glu Lys Pro Ser Gly Gln Pro Ser Leu Lys Lys Ile Ile Leu|

433  TCC CGC AAA AAG AGA AGT GGA CGT CAC AGA TTT GAT CCA TTC TGT TGT GAA GTA ATT TGT GAC GAT
 93  Ser Arg Lys Lys Arg Ser Gly Arg His Arg Phe Asp Pro Phe Cys Cys Glu Val Ile Cys Asp Asp
     A-chain 499  GGA ACT TCA GTT AAA TTA TGT ACA TAG TAGAGTAATCATGGACTGGACATCTCATCCATTCTCATATGTATTCTCAAT
115  Gly Thr Ser Val Lys Leu Cys Thr ***

527  GACAAATTCACTGATGCCCAATTAAATGATTGCTGTTT   3' ...

FIGURE 2B

PROTEIN CALLED EPIL/PLACENTIN, PROCESS FOR THE PREPARATION OF THIS PROTEIN AND PHARMACEUTICAL COMPOSITION CONTAINING SUCH, DNA CODING FOR SAID PROTEIN

This application is a divisional of application Ser. No. 09/174,465, filed Oct. 19, 1998, now U.S. Pat. No. 6,180,364 which is a divisional of application Ser. No. 08/482,842, filed Jun. 7, 1995 now U.S. Pat. No. 5,910,480.

FIELD OF THE INVENTION

The present invention concerns a new protein called placentin of EPIL, its analogs, the procedures for their preparation and their applications.

BACKGROUND OF THE INVENTION

Insulin, IGF-1, IGF-2 and relaxin belong to a family of peptide hormones having certain common structures and functions, particularly their influence upon cell proliferation, development, differentiation and metabolism.

Insulin is well known as being an endocrine pancreatic hormone regulating energy metabolism. Growth factors of insulin-IGF-1 type are growth promoting peptides involved in endocrine, paracrine and autocrine regulation of cell growth and which are expressed in numerous tissues. IGF-2 has similar properties but is expressed in higher quantities during the prenatal period and is considered as being a fetal growth factor.

Relaxin induces remodeling of connective tissue in the reproductive tract and inhibits uterine contractions. Its functional role in the brain, where extensive expression has been obtained, remains to be elucidated.

Recently, Ley-I-Ls were added to this family which are currently cloned in cDNA form and whose biological activity remains to be determined. This peptide family commonly presents structural characteristics defined by the position of different cysteines essential for the formation of a tertiary structure.

Insulin, which is the prototype for this family, comprises two peptide A and B chains connected to disulfide bridges. It is coded by a mRNA which is translated into preproinsulin. The peptide signal, like the connecting C peptide, are excised by post-translational modification; this also applies to relaxin although the IGFs are matured differently without elimination of the C peptide and remain as a single chain. It has been shown that all the members of this family attach themselves to cell surface receptors. These receptors have been identified by molecular cloning and characterized in detail for insulin and IGF. They belong to the superfamily of tyrosine protein kinase receptors (Tyr-PK receptors) which comprises growth factor receptors and their oncogene analogs such as c-neu/erb-B-2 (EGF receptor), c-met (hepatocyte growth factor receptor), fms (CSF-1 receptor) and trk (NGF receptor).

The transduction route of the intracellular signal for these receptors is characterized by tyrosine-kinase activity which produces autophosphorylation of the tyrosine residues on the receptor followed by a chain of events corresponding to phosphorylations. This includes, in particular, the activation of IRS-1 (particularly for insulin and IGF), P13K, Shc, GBRZ, Sos, Ras, Raf and the kinase mitogenesis activating protein (MAP) especially when the cascade of phosphorylation affects different cell processes such as transcription. The pleiotropic physiological effects of this cascade of signals are generally the subject of intense research.

BRIEF DESCRIPTION OF THE DRAWINGS

FIGS. 1A and 1B depict a DNA sequence (SEQ ID NO: 1) and corresponding amino acid sequence (SEQ ID NO: 2) for EPIL/placentin.

FIGS. 2A and 2B depict the detailed structure of EPIL/placentin (SEQ ID NO: 2) including the signal sequence (position −17 to −1), the B chain (position 1 to 41), the C peptide (position 42–92), and the A chain (position 93–122).

DETAILED DESCRIPTION OF THE INVENTION

The present invention concerns, more particularly, a new molecule of this insulin family which is called hereinafter placentin or EPIL (Early Placenta Insulin-Like peptide) whose amino acid sequence and the DNA sequence which codes for this protein corresponds to the ID 1 sequence.

EPIL/Placentin was isolated from a cDNA bank of cytotrophoblastic cells prepared from placenta taken during the first trimester of pregnancy. Northern blot analysis (performed on very wide sampling of normal tissues) revealed detectable RNA levels only in placental tissue.

The amino acid sequence obtained shows an arrangement of cysteine residues for protein according to the invention that is characteristic of the insulin family.

The treatment of target cells with media fed with cell cultures expressing the recombinant protein seems to induce a pattern of tyrosine phosphorylation similar to that observed after treatment with insulin.

Finally, EPIL/placentin induces DNA synthesis.

This is why the present invention concerns, more particularly, a protein called EPIL/placentin, a protein with a formula corresponding to sequence ID 1, also represented in FIG. 1, and its analogs showing placentin-type activity and obtained by deletion and/or substitution.

On sequence ID1, the structure of EPIL/placentin corresponds to the amino acid structure following methionine at position 36 as far as the amino acid at position 174.

The references to the DNA sequences of EPIL/placentin correspond to this sequence.

The nucleic sequences existing before the first presumed ATG (underlined) and after the stop codon are in small letters.

EPIL/Placentin analogs are proteins or peptides which have high amino acid homology, particularly over 60% homology, preferably 80%, with the compound corresponding to sequenced ID 1, which could be obtained by deletion or by substitution while preserving the essential characteristics of EPIL/placentin. These analogs shall sometimes be called "EPIL/placentin-type compounds".

In particular, the present invention concerns fragments which show certain epitopes characteristic of EPIL/placentin activity, in particular EPIL/placentin-type proteins which have at least the first 20 amino acids of the N-terminal extremity of sequence ID 1.

The present invention evidently concerns EPIL/placentin or its analogs in glycosylated or non-glyosylated form and the proteins with or without the disulfide bridges of the original protein. Indeed, this protein may be prepared by extraction using biological samples but shall be preferably obtained via techniques using genetic engineering and its secondary structures may vary in accordance with the host organism.

The invention also concerns a molecule chosen among:

(a) the DNA sequence of the ID 1 sequence, (b) DNA sequences likely to hybridize to the preceding sequence and which code for a EPIL/placentin-type polypeptide, and (c) DNA sequences which taking into account the genetic code correspond to sequences (a) or (b) and which code for a EPIL/placentin-type polypeptide.

In particular, the invention concerns the DNA sequence corresponding to sequence ID 1.

Evidently, the DNA sequences previously mentioned may be genomic or genomic-type sequences, that is to say that certain elements may be separated by introns which will be excised to lead to the expression of mature EPIL/placentin.

The preceding DNA sequences may be incorporated into cloning or expression vectors of EPIL/placentin or its analogs, preferably under the control of elements assuring their expression in a defined host cell.

The systems of expression in prokaryotic or eukaryotic cells are well known to men of the art. These may in particular concern systems of plasmid type or viral type comprising promotors assuring expression in the host cell and also provided with the necessary terminal elements.

But they may also concern integration vectors which may comprise their own system of expression or else be designed to integrate into the chromosomes in places where they come under the promotion of a chromosome promotor, in particular in the case of prokaryotic cells, using the homologous recombination technique.

The present invention also concerns host cells characterized in that they comprise a self-replicating vector expressing EPIL/placentin or a EPIL/placentin analog in accordance with the invention or a DNA sequence in accordance with the invention incorporated into a chromosome and expressing EPIL/placentin or a EPIL/placentin analog.

As previously indicated, these may be eukaryotic cells, in particular mammalian cells of CHO cell type, or cultured cells of other types more appropriate to the preparation of EPIL/placentin in its mature form; but it is also possible to contemplate using bacterial cells for example: in this case it may be appropriate to subject the protein obtained to additional modifications.

These techniques are again known to men of the art and shall not be described more fully, except within the context of certain examples below.

The cells thus transformed by a self-replicating vector expressing the protein or having integrated the sequence expressing the protein in its chromosomes may be used by culture in a process permitting the preparation of EPIL/placentin or its analogs.

This particularly concerns a process for the preparation of EPIL/placentin or its analogs characterized by the culturing of cells from which EPIL/placentin or its analogs shall be extracted either directly or from the culture medium.

EPIL/Placentin may in particular be extracted by immunopurification.

The present invention also concerns recombination products obtained through the previously performed process.

In certain cases, the protein may be prepared in fused form, in particular when a peptide-type analog of EPIL/placentin is involved, or when fusion with this protein provides easier access to the action site of EPIL/placentin or its analogs, or when, in certain cases, this protein can be used to deceive certain natural systems by giving the protein of interest longer life.

Finally, the present invention relates to pharmaceutical compositions using EPIL/placentin or its analogs as an active ingredient.

As indicated, EPIL/placentin has multiple activities, in particular it may, like other type 1 human growth factors, offer cardiac-related activity, in particular for the treatment and prevention of certain heart disorders such as acute cardiac failure.

This protein or some of its analogs may offer growth factor and lactation type activity. Also, the products may be used in the regeneration process of nerve, muscle, skin or bone tissues, especially in degenerative or endocrine pathologies, traumatic lesions or viral illnesses.

Finally, EPIL/placentin or its analogs may offer action in connection with the control of all phenomena relating to conception in man or animal.

The present invention also concerns antibodies and more particularly specific monoclonal antibodies of EPIL/placentin or its analogs, and an in vitro diagnosis method which uses EPIL/placentin or its analogs and/or corresponding antibodies to detect abnormal levels of EPIL/placentin in samples that may or may not be physiological.

DNA fragments corresponding to the previously mentioned sequences may be integrated into "sense" or "antisense" treatment strategy; EPIL/placentin or its analogs could be integrated into a strategy targeting certain pharmaceutically active molecules towards receptors of EPIL/placentin or is analogs.

The detailed structure of EPIL/placentin [SEQ ID NO:2] called EPIL corresponds to sequence of FIG. 2, that is to say a peptide signal at position −17 to −1, a B chain 1 to 41, a connecting C peptide from 42 to 92 then an A chain from 93 to 122.

This structure relates EPIL to proinsulin or prorelaxin.

In particular, the position of the disulfide bridges must lead to an insulin-type three-dimensional structure.

Other characteristics and advantages of the present invention will appear on reading the following examples making reference to sequences ID 1 and FIG. 2 (SEQ ID NOS: 4–14) corresponding to the sequence of EPIL/placentin and of the human gene coding for this protein.

EXAMPLES

The identification of EPIL/placentin is the outcome of specific research seeking to determine the molecules involved in cell growth and/or in neoplasic processes.

Although placenta is a normal tissue, its constituting cells have numerous properties in common with neoplasic cells, in particular with invasive, highly mitotic cytotrophoblasts which may penetrate the maternal tissue. These trophoblasts are an inexhaustible source of growth factors, hormones and growth factor receptors in particular.

Current studies show that the genes preferably expressed in trophoblastic cells may also be preferably expressed in neoplasic cells.

However taking into account that placenta, and in particular trophoblasts, remain under full control during normal pregnancy, the trophoblastic molecules corresponding to this control are highly interesting candidates as anticancerous agents or likely to control the cancerisation process.

This is why the isolation method used is a cDNA subtraction method having recourse to PCR technology on young trophoblasts. This permitted the detection of genes which are overexpressed in these cells and which may play a role in cellular growth and regulation.

MATERIAL AND METHODS

Tissues

Placentas of 5 to 12 weeks, full term placentas and surgical samples of normal and tumorous tissues were refrigerated immediately (within 10 minutes after surgery) and preserved in liquid nitrogen until RNA preparation. These tissue collections were obtained and used in accordance with protocols approved by the Committees of the different hospitals.

Cells

The human cell lines used throughout this study and their histological origins are as follows: gestational choriocarcinoma (JAr and JEG-3); hepatocellular carcinoma (PLC/PRF/5 and Hep G2); colon adenocarcinoma (LSI80); ovarian carcinoma (OVI/p, OVIVCR), the OVI/VCR cell line is derived from OVI/p and is resistant to vincristin; epidermoid carcinoma (A431); lung carcinoma (A427); epithelioid carcinoma of the cervix (HeLa); mammary carcinoma (McF7, MDA-MB-361, SK-BR-3, BT-20 and BT-474); mammary cells transformed by SV-40 (HBL-100): neuroblastoma cell line (SHSY-5Y); normal fibroblast cell line (CCL-137).

All these cell lines being available to ATCC with the exception of IGR/OVI (OVI/p) and OVI/VCR.

These cell lines are cultured in a DMEM or RPMI-1460 medium (Gibco-BRL Laboratories, Gaithersburg, Mass.) supplemented with 10% fetal calf serum inactivated by heat, 10 μm non essential amino acids, 4 mM glutamin, 100 U/ml penicillin and 100 μg/ml streptomycin at 37 iC with 5% CO2.

Isolation of the Cytotrophoblasts

The cytotrophoblasts are purified as described by Kliman et al. Endocrinology, 118: 1567–1582, 1986. Briefly, the villi tissue of first trimester placenta are dispersed with trpysin and deoxyribonuclease-1. The dispersed cells are then purified through a 5–70% Percoll gradient (Pharmacia). The 1 040–1 060 g/ml density band is collected. Microscropic examination shows that it comprises cytotrophoblastic cells with less than 5% contamination with non-trophoblastic cells such as macrophages, fibroblasts and endothelial cells.

Preparation of RNA

Total RNA is prepared from preconfluent cell cultures or refrigerated tissues using guanidinine isothiocyanate and ultracentrifugation on a cesium chloride gradient by adapting the protocol described by Chirgwin et al. The polysome RNAs associated with the endoplasmic reticulum membranes (MB-RNA) are purified as described previously. After trypsination and purification through a Percoll gradient, the cytotrophoblastic cells are homogenized, then the MB-RNAs are isolated on a sucrose gradient to which is added a vanadyl ribonucleoside complex as ribonuclease inhibitor.

cDNA synthesis and PCR amplification 0.1 μg MB-RNA are dissolved in 5 μl DEPC treated water and denatured with 0.1 M MeHgOH and β-mercaptoethanol. The first cDNA strand is synthesized with the reverse transcriptase of avian myoblastosis virus (Invitrogen kit, San Diego) using the modified dT primer indicated below (Frohman et al. Proc. Natl. Acad. Sci. USA, 85: 8998–9002, 1988). The RNA-cDNA heteroduplexes of size ranging from 0.5 to 2 kb are electroeluted after migration in 2% agarose gel. A dG oligo tail is added to the 3' end of the first cDNA strand with the terminal deoxynucleotide transferase and the RNA is eliminated by alkaline hydrolysis. The cDNAs are amplified with non specific primers including restriction sites for NotI and SalI enzymes.

The sequence (SEQ ID NO: 15) of the T primer used for reverse transcription and PCR is as follows:

5'-GACTCGAGTCGACATCGATTTTTTTTTTTTTTTTT-3'

The C primer (SEQ ID NO: 16) is identical to that described by Loh et al., (Science, 243: 217–220, 1989):

5'GCATCGGCGCGGCCGCGGAGGCCCCCCCCCCCCCC-3'

The reaction mixture comprises 1.25 mM of each of the 4 triphosphate desoxyribonucleotides, 0.5 μM of each primer and 2.5 units of Taq polymerase in 50 mM Kcl-10 mM Tris-HCl (pH 8.3)—3.5 mM MgCl2-0.01% gelatin. Amplification is carried out in a thermal cycler for 25 cycles of 20 seconds at 94 iC, 30 seconds at 55 iC and 1 minute at 72 iC. The products are loaded on 1% agarose gel at low fusion. The 0.5–2 kb region is then excised and reamplified under the same conditions. The products are precipitated, fully digested with NotI and SalI, the sizes are selected as previously and electroeluted from agarose, precipitated and quantified.

The total cDNA of full term placenta and T lymphocytes activated with phytohemagglutinin and cultivated for several days in the presence of IL2 was prepared using a double strand cDNA synthesis method.

Construction of the subtracted cDNA bank

Subtraction hybridization is performed as described by Klickstein (Klickstein et al. Current protocols in molecular biology, pp 5.8.9.–5.8.15 Wiley Interscience, 1989). 0.2 μg cDNA from cytotrophoblastic cells amplified by PCR are left to digest with NotI and SalI, mixed with 8 μg cDNA of activated T lymphocytes and 8 μg cDNA of full term placenta digested with AluI and RsaI, dissolved in 40 μl hybridization buffer (50% deionized formamide; 10 mM sodium phosphate buffer, pH 7; 5×SSC; 0.1% SDS; 10 mM EDTA), denatured for 5 minutes at 98 iC and incubated for 24 hours at 37 iC.

The sequences common to target and competitor are collected to form duplexes between the short fragments (Alu/Rsa, competitor) and the long fragments (Not/Sal of the target) by inhibiting the formation of cohesive ends. Complementary cDNA strands specifically expressed in the young cytotrophoblasts permit the regeneration of the NotI and SalI cohesive ends for unidirectional cloning in the pBSKII sites+vector phagemid (Stratagene).

Bank sifting

The subtracted cDNA bank is spread over a gelose culture medium and the recombinant colonies are collected and cultured in the LB medium then amplified by PCR. The plasmid DNAs, prepared by the boiled minipreparation method (Del Sal G. et al. Nucleic Acids Res., 16: 9878, 1988) and digested with NotI and SalI or the insert products amplified by PCR using the original primers, are analyzed by Southern blotting on 1.2% agarose gels. The average size of inserts is between 500 and 1 000 nucleotides. The gels are transferred in duplicate onto nylon membranes (Hybond N, Amersham) in an alkaline buffer. The probes used for hybridization are total cDNAs synthesized from young placentas, full term placentas and activated T lymphocytes 32P-labeled (Amersham) by random multiple priming. Hybridization is carried out for 18 hours at 42 iC followed by stringent washing in 0.1×SSC at 50 iC and autoradiography.

Northern blot analysis

5 μg of total RNA taken from different tissues and cell lines are analyzed on 1% agarose gel containing 2.2 M of formaldehyde. On completion of electrophoresis, the gel is rinsed with bi-distilled water and treated with 10×SSC for 30 minutes. The RNA is then transferred to a reinforced nitrocellulose membrane (Schleicher & Schuell, Dassel) in the 20×SSC transfer buffer for 18 hours. The transferred RNAs are fixed to the membranes by UV radiation before hybridization. The probes used to hybridize the membranes are excised inserts 32P-labeled by random multiple priming, or single strand probes generated by PCR using a universal antisense primer. Hybridization is carried out overnight at 42 iC followed by stringent washing in 0.1×SSC at 50 iC and autoradiography.

DNA sequencing and analysis

The plasmid DNAs are prepared using the boiled mini-preparation method. DNA sequencing is performed with the Sequenase kit, version 2.0 (U.S. Biochemical). The primers are either universal M13, T3, or T7 primers or specific internal primers. Reaction products are analyzed on gels containing 6% acrylamide and 50% urea. The sequences obtained are compared with the sequences of the different data banks.

Analysis

The clones which do not give any hybridization signal with standardized probes are analyzed by partial sequencing and comparison with these data banks.

One of the clones corresponding to EPIL/placentin corresponds to the amino acid sequence corresponding to sequence ID 1.

Total RNA and polyA samples prepared from normal or transformed cell lines and from corresponding tissues are subjected to Northern blotting with labeled, single strand, antisense EPIL/placentin cDNA probes. Hybridization signals are detected solely in the placentas, especially early pregnancy placentas and are practically non-existent in the other tissues as shown in the table given below (Table 1):

TABLE 1

| | |
|---|---|
| YOUNG PLACENTA | ++++ |
| FULL TERM PLACENTA | ++ |
| NORMAL LIVER | − |
| TUMOROUS LIVER | − |
| NORMAL BLADDER | − |
| TUMOROUS BLADDER | − |
| NORMAL OMENTUM | − |
| TUMOROUS OMENTUM | − |
| NORMAL ESOPHAGUS | − |
| TUMOROUS ESOPHAGUS | − |
| NORMAL COLON | − |
| TUMOROUS COLON | − |

TABLE 1-continued

| | |
|---|---|
| NORMAL STOMACH | − |
| NORMAL CERVIX UTERI | − |
| NORMAL ENDOMETRIUM | − |
| NORMAL OVARY | − |
| TUMOROUS BREAST | − |
| TUMOROUS GANGLION | − |
| NORMAL SPLEEN | − |
| NORMAL RECTUM | − |
| TUMOROUS RECTUM | − |
| NORMAL FALLOPIAN TUBE | − |
| NORMAL SKIN | − |
| NORMAL MYOMETRIUM | − |
| NORMAL ADRENAL GLAND | − |
| NORMAL THYROID | − |
| TUMOROUS THYROID | − |

Studies carried out on murine and simian products show analogies indicating significant functional similarities between species.

EPIL/Placentin expression

For the eukaryotic expression of EPIL/placentin, cDNA was inserted into the pBK-CMV expression vector in the sense and antisense position.

Two cell types were used to examine the possible effects of post-translational modifications inherent to cell types. COS-7 monkey kidney cells were transfected by DEAE for transient expression while the human trophoblastic cells transformed by SV40 (3AsubE) were transfected by CaPO4 for stable, transient expression.

The COS-7 and 3AsubE cells do not express any detectable level of EPIL/placentin mRNA with northern blot. The transfected cells are fed with serum-free culture medium.

The media fed with sense or antisense transfected cells are analyzed to detect the presence of recombinant proteins.

The biological activity of the recombinant protein is analyzed on different target cells considering that the specific receptors may exist or that the protein may attach itself to other receptors for molecules of proximal structure as was observed for insulin and IGF.

Preliminary results suggest that EPIL/placentin would induce tyrosine phosphorylation of cellular proteins and would have biological activity on trophoblastic cells growth.

What is claimed is:

1. An antibody that binds to EPIL/placentin consisting of SEQ ID NO:2 or a fragment thereof selected from the group consisting of SEQ ID NO:8, SEQ ID NO:10 and SEQ ID NO:12.

2. The antibody of claim 1, wherein said antibody binds to glycosylated EPIL/placentin.

3. A monoclonal antibody that binds to EPIL/placentin consisting of SEQ ID NO:2 or a fragment thereof selected from the group consisting of SEQ ID NO:8, SEQ ID NO:10 and SEQ ID NO:12.

4. The monoclonal antibody of claim 3, wherein the antibody binds to glycosylated EPIL/placentin.

* * * * *

SEQUENCE LISTING

```
<160> NUMBER OF SEQ ID NOS: 16

<210> SEQ ID NO 1
<211> LENGTH: 615
<212> TYPE: DNA
<213> ORGANISM: Unknown
<220> FEATURE:
<221> NAME/KEY: CDS
<222> LOCATION: (1)..(615)
<223> OTHER INFORMATION: Description of Unknown Organism:EPIL - Early
      Placenta Insulin-Like Peptide

<400> SEQUENCE: 1 agt ctg gag ccc aga agg gac aca cca gca cag tct ggt agg cta cag      48
Ser Leu Glu Pro Arg Arg Asp Thr Pro Ala Gln Ser Gly Arg Leu Gln
  1               5                  10                  15 cag caa gtc tct aaa gaa agg ctg aga aca ccc aga aca gga gag ttc      96
Gln Gln Val Ser Lys Glu Arg Leu Arg Thr Pro Arg Thr Gly Glu Phe
```

```
                    20                  25                  30
agg tcc agg atg gcc agc ctg ttc cgg tcc tat ctg cca gca atc tgg      144
Arg Ser Arg Met Ala Ser Leu Phe Arg Ser Tyr Leu Pro Ala Ile Trp
            35                  40                  45 ctg ctg ctg agc caa ctc ctt aga gaa agc cta gca gca gag ctg agg      192
Leu Leu Leu Ser Gln Leu Leu Arg Glu Ser Leu Ala Ala Glu Leu Arg
    50                  55                  60 gga tgt ggt ccc cga ttt gga aaa cac ttg ctg tca tat tgc ccc atg      240
Gly Cys Gly Pro Arg Phe Gly Lys His Leu Leu Ser Tyr Cys Pro Met
65                  70                  75                  80 cct gag aag aca ttc acc acc acc cca gga ggg tgg ctg ctg gaa tct      288
Pro Glu Lys Thr Phe Thr Thr Thr Pro Gly Gly Trp Leu Leu Glu Ser
                85                  90                  95 gga cgt ccc aaa gaa atg gtg tca acc tcc aag aac aaa gat gga caa      336
Gly Arg Pro Lys Glu Met Val Ser Thr Ser Lys Asn Lys Asp Gly Gln
            100                 105                 110 gcc tta ggt acg aca tca gaa ttc att cct aat ttg tca cca gag ctg      384
Ala Leu Gly Thr Thr Ser Glu Phe Ile Pro Asn Leu Ser Pro Glu Leu
    115                 120                 125 aag aaa cca ctg tct gaa ggg cag cca tca ttg aag aaa ata ata ctt      432
Lys Lys Pro Leu Ser Glu Gly Gln Pro Ser Leu Lys Lys Ile Ile Leu
130                 135                 140 tcc cgc aaa aag aga agt gga cgt cac aga ttt gat cca ttc tgt tgt      480
Ser Arg Lys Lys Arg Ser Gly Arg His Arg Phe Asp Pro Phe Cys Cys
145                 150                 155                 160 gaa gta att tgt gac gat gga act tca gtt aaa tta tgt aca tag tag      528
Glu Val Ile Cys Asp Asp Gly Thr Ser Val Lys Leu Cys Thr
                165                 170                 175 agt aat cat gga ctg gac atc tca tcc att ctc ata tgt att ctc aat      576
Ser Asn His Gly Leu Asp Ile Ser Ser Ile Leu Ile Cys Ile Leu Asn
            180                 185                 190 gac aaa ttc act gat gcc caa tta aat gat tgc tgt tta                  615
Asp Lys Phe Thr Asp Ala Gln Leu Asn Asp Cys Cys Leu
    195                 200                 205

<210> SEQ ID NO 2
<211> LENGTH: 139
<212> TYPE: PRT
<213> ORGANISM: Unknown
<220> FEATURE:
<223> OTHER INFORMATION: Description of Unknown Organism:EPIL - Early
      Placenta Insulin-Like Peptide

<400> SEQUENCE: 2

Met Ala Ser Leu Phe Arg Ser Tyr Leu Pro Ala Ile Trp Leu Leu Leu
                5                   10                  15

Ser Gln Leu Leu Arg Glu Ser Leu Ala Ala Glu Leu Arg Gly Cys Gly
            20                  25                  30

Pro Arg Phe Gly Lys His Leu Leu Ser Tyr Cys Pro Met Pro Glu Lys
        35                  40                  45

Thr Phe Thr Thr Thr Pro Gly Gly Trp Leu Leu Glu Ser Gly Arg Pro
    50                  55                  60

Lys Glu Met Val Ser Thr Ser Lys Asn Lys Asp Gly Gln Ala Leu Gly
65                  70                  75                  80

Thr Thr Ser Glu Phe Ile Pro Asn Leu Ser Pro Glu Leu Lys Lys Pro
                85                  90                  95

Leu Ser Glu Gly Gln Pro Ser Leu Lys Lys Ile Ile Leu Ser Arg Lys
            100                 105                 110

Lys Arg Ser Gly Arg His Arg Phe Asp Pro Phe Cys Cys Glu Val Ile
```

Cys Asp Asp Gly Thr Ser Val Lys Leu Cys Thr
        130                 135

<210> SEQ ID NO 3
<211> LENGTH: 29
<212> TYPE: PRT
<213> ORGANISM: Unknown
<220> FEATURE:
<223> OTHER INFORMATION: Description of Unknown Organism:EPIL - Early
      Placenta Insulin-Like Peptide

<400> SEQUENCE: 3

Ser Asn His Gly Leu Asp Ile Ser Ser Ile Leu Ile Cys Ile Leu Asn
 1               5                  10                  15

Asp Lys Phe Thr Asp Ala Gln Leu Asn Asp Cys Cys Leu
            20                  25

<210> SEQ ID NO 4
<211> LENGTH: 934
<212> TYPE: DNA
<213> ORGANISM: Unknown
<220> FEATURE:
<223> OTHER INFORMATION: Description of Unknown Organism:EPIL - Early
      Placenta Insulin-Like peptide

<400> SEQUENCE: 4
aggtcagttc tattttatt tcatctaagc aaaggacatt aaaaattacc attattttag      60
taagcataaa aatagtatta caggaggaaa gttaagaaaa agaagtagaa caaccaaatt    120
caaaacaagc aaagtgcagc agcacattgg gagcaaagag ggatatgaga gtgtgggtag    180
ggcaagtagg gagactaaat aagaactgag ggagaaagtt ccttgtaggt gggtgggaaa    240
ggggtggact gacaccattg acgccaaagc tgagtatagc cctaagccaa ataaatgcct    300
gatgaaggca tgcagaaagc agtctggagc ccagaaggga cacaccagca cagtctggta    360
ggctacagca gcaagtctct aaagaaaggc tgagaacacc cagaacagga gagttcaggt    420
ccaggatggc cagcctgttc cggtcctatc tgccagcaat ctggctgctg ctgagccaac    480
tccttagaga aagcctagca gcagagctga ggggatgtgg tccccgattt ggaaaacact    540
tgctgtcata ttgcccccatg cctgagaaga cattcaccac caccccagga gggtggctgc    600
tggaatctgg acgtcccaaa gaatggtgt caacctccaa caacaaagat ggacaagcct    660
taggtacgac atcagaattc attcctaatt tgtcaccaga gctgaagaaa ccactgtctg    720
aagggcagcc atcattgaag aaaataatac tttcccgcaa aaagagaagt ggacgtcaca    780
gatttgatcc attctgttgt gaagtaattt gtgacgatgg aacttcagtt aaattatgta    840
catagtagag taatcatgga ctggacatct catccattct catatgtatt ctcaatgaca    900
aattcactga tgcccaatta aatgattgct gttt                                934

<210> SEQ ID NO 5
<211> LENGTH: 157
<212> TYPE: DNA
<213> ORGANISM: Unknown
<220> FEATURE:
<221> NAME/KEY: CDS
<222> LOCATION: (107)..(157)
<223> OTHER INFORMATION: Description of Unknown Organism:EPIL - Early
      Placenta Insulin-Like peptide

<400> SEQUENCE: 5
cagtctggag cccagaaggg acacaccagc acagtctggt aggctacagc agcaagtctc     60

```
taaagaaagg ctgagaacac ccagaacagg agagttcagg tccagg atg gcc agc        115
                                                    Met Ala Ser
                                                      1 ctg ttc cgg tcc tat ctg cca gca atc tgg ctg ctg ctg agc               157
Leu Phe Arg Ser Tyr Leu Pro Ala Ile Trp Leu Leu Leu Ser
     5                  10                  15
```

<210> SEQ ID NO 6
<211> LENGTH: 17
<212> TYPE: PRT
<213> ORGANISM: Unknown
<220> FEATURE:
<223> OTHER INFORMATION: Description of Unknown Organism:EPIL - Early
      Placenta Insulin-Like Peptide

<400> SEQUENCE: 6

```
Met Ala Ser Leu Phe Arg Ser Tyr Leu Pro Ala Ile Trp Leu Leu Leu
 1               5                  10                  15

Ser
```

<210> SEQ ID NO 7
<211> LENGTH: 123
<212> TYPE: DNA
<213> ORGANISM: Unknown
<220> FEATURE:
<221> NAME/KEY: CDS
<222> LOCATION: (1)..(123)
<223> OTHER INFORMATION: Description of Unknown Organism:EPIL - Early
      Placenta Insulin-Like peptide

<400> SEQUENCE: 7

```
caa ctc ctt aga gaa agc cta gca gca gag ctg agg gga tgt ggt ccc       48
Gln Leu Leu Arg Glu Ser Leu Ala Ala Glu Leu Arg Gly Cys Gly Pro
 1               5                  10                  15 cga ttt gga aaa cac ttg ctg tca tat tgc ccc atg cct gag aag aca       96
Arg Phe Gly Lys His Leu Leu Ser Tyr Cys Pro Met Pro Glu Lys Thr
                20                  25                  30 ttc acc acc acc cca gga ggg tgg ctg                                  123
Phe Thr Thr Thr Pro Gly Gly Trp Leu
            35                  40
```

<210> SEQ ID NO 8
<211> LENGTH: 41
<212> TYPE: PRT
<213> ORGANISM: Unknown
<220> FEATURE:
<223> OTHER INFORMATION: Description of Unknown Organism:EPIL - Early
      Placenta Insulin-Like Peptide

<400> SEQUENCE: 8

```
Gln Leu Leu Arg Glu Ser Leu Ala Ala Glu Leu Arg Gly Cys Gly Pro
 1               5                  10                  15

Arg Phe Gly Lys His Leu Leu Ser Tyr Cys Pro Met Pro Glu Lys Thr
                20                  25                  30

Phe Thr Thr Thr Pro Gly Gly Trp Leu
            35                  40
```

<210> SEQ ID NO 9
<211> LENGTH: 153
<212> TYPE: DNA
<213> ORGANISM: Unknown
<220> FEATURE:
<221> NAME/KEY: CDS
<222> LOCATION: (1)..(153)
<223> OTHER INFORMATION: Description of Unknown Organism:EPIL - Early Placenta Insulin-Like peptide

<400> SEQUENCE: 9

```
ctg gaa tct gga cgt ccc aaa gaa atg gtg tca acc tcc aac aac aaa      48
Leu Glu Ser Gly Arg Pro Lys Glu Met Val Ser Thr Ser Asn Asn Lys
 1               5                  10                  15 gat gga caa gcc tta ggt acg aca tca gaa ttc att cct aat ttg tca      96
Asp Gly Gln Ala Leu Gly Thr Thr Ser Glu Phe Ile Pro Asn Leu Ser
                20                  25                  30 cca gag ctg aag aaa cca ctg tct gaa ggg cag cca tca ttg aag aaa     144
Pro Glu Leu Lys Lys Pro Leu Ser Glu Gly Gln Pro Ser Leu Lys Lys
                35                  40                  45 ata ata ctt                                                         153
Ile Ile Leu
        50
```

<210> SEQ ID NO 10
<211> LENGTH: 51
<212> TYPE: PRT
<213> ORGANISM: Unknown
<220> FEATURE:
<223> OTHER INFORMATION: Description of Unknown Organism:EPIL - Early
      Placenta Insulin-Like Peptide

<400> SEQUENCE: 10

```
Leu Glu Ser Gly Arg Pro Lys Glu Met Val Ser Thr Ser Asn Asn Lys
 1               5                  10                  15

Asp Gly Gln Ala Leu Gly Thr Thr Ser Glu Phe Ile Pro Asn Leu Ser
                20                  25                  30

Pro Glu Leu Lys Lys Pro Leu Ser Glu Gly Gln Pro Ser Leu Lys Lys
                35                  40                  45

Ile Ile Leu
        50
```

<210> SEQ ID NO 11
<211> LENGTH: 93
<212> TYPE: DNA
<213> ORGANISM: Unknown
<220> FEATURE:
<221> NAME/KEY: CDS
<222> LOCATION: (1)..(93)
<223> OTHER INFORMATION: Description of Unknown Organism:EPIL - Early
      Placenta Insulin-Like peptide

<400> SEQUENCE: 11

```
tcc cgc aaa aag aga agt gga cgt cac aga ttt gat cca ttc tgt tgt      48
Ser Arg Lys Lys Arg Ser Gly Arg His Arg Phe Asp Pro Phe Cys Cys
 1               5                  10                  15 gaa gta att tgt gac gat gga act tca gtt aaa tta tgt aca tag          93
Glu Val Ile Cys Asp Asp Gly Thr Ser Val Lys Leu Cys Thr
                20                  25                  30
```

<210> SEQ ID NO 12
<211> LENGTH: 30
<212> TYPE: PRT
<213> ORGANISM: Unknown
<220> FEATURE:
<223> OTHER INFORMATION: Description of Unknown Organism:EPIL - Early
      Placenta Insulin-Like Peptide

<400> SEQUENCE: 12

```
Ser Arg Lys Lys Arg Ser Gly Arg His Arg Phe Asp Pro Phe Cys Cys
 1               5                  10                  15

Glu Val Ile Cys Asp Asp Gly Thr Ser Val Lys Leu Cys Thr
```

```
<210> SEQ ID NO 13
<211> LENGTH: 48
<212> TYPE: DNA
<213> ORGANISM: Unknown
<220> FEATURE:
<223> OTHER INFORMATION: Description of Unknown Organism:EPIL - Early
      Placenta Insulin-Like peptide

<400> SEQUENCE: 13
gtgagagccc tggactacca aacaatcaga atgagggctg aaaaaaca                48

<210> SEQ ID NO 14
<211> LENGTH: 47
<212> TYPE: DNA
<213> ORGANISM: Unknown
<220> FEATURE:
<223> OTHER INFORMATION: Description of Unknown Organism:EPIL - Early
      Placenta Insulin-Like peptide

<400> SEQUENCE: 14
acatgaatgt ttttcctcac ctttcattcc tctcttttac ttcacag                 47

<210> SEQ ID NO 15
<211> LENGTH: 35
<212> TYPE: DNA
<213> ORGANISM: Unknown
<220> FEATURE:
<223> OTHER INFORMATION: Description of Unknown Organism:EPIL - Early
      Placenta Insulin-Like peptide

<400> SEQUENCE: 15
gactcgagtc gacatcgatt tttttttttt ttttt                              35

<210> SEQ ID NO 16
<211> LENGTH: 35
<212> TYPE: DNA
<213> ORGANISM: Unknown
<220> FEATURE:
<223> OTHER INFORMATION: Description of Unknown Organism:EPIL - Early
      Placenta Insulin-Like peptide

<400> SEQUENCE: 16
gcatcggcgc ggccgcggag gcccccgccc ccccc                              35
```